United States Patent
Grodzki et al.

(10) Patent No.: US 10,620,285 B2
(45) Date of Patent: Apr. 14, 2020

(54) METHOD AND MAGNETIC RESONANCE APPARATUS FOR MONITORING AN INTERVENTIONAL PROCEDURE CONDUCTED WITH AN INTERVENTION TOOL

(71) Applicant: Siemens Healthcare GmbH, Erlangen (DE)

(72) Inventors: David Grodzki, Erlangen (DE); Rainer Schneider, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 16/162,725

(22) Filed: Oct. 17, 2018

(65) Prior Publication Data
US 2019/0113589 A1 Apr. 18, 2019

(30) Foreign Application Priority Data
Oct. 17, 2017 (DE) .......................... 10 2017 218 524

(51) Int. Cl.
| | |
|---|---|
| G01R 33/28 | (2006.01) |
| G01R 33/563 | (2006.01) |
| G01R 33/54 | (2006.01) |
| G01R 33/483 | (2006.01) |
| A61B 1/045 | (2006.01) |
| A61B 1/05 | (2006.01) |
| G01R 33/56 | (2006.01) |

(52) U.S. Cl.
CPC ............ *G01R 33/543* (2013.01); *A61B 1/045* (2013.01); *A61B 1/05* (2013.01); *G01R 33/287* (2013.01); *G01R 33/4838* (2013.01); *G01R 33/5608* (2013.01); *G01R 33/5635* (2013.01)

(58) Field of Classification Search
CPC .............. G01R 33/543; G01R 33/5608; G01R 33/287; A61B 1/045; A61B 1/05
USPC ........................................................ 324/307
See application file for complete search history.

(56) References Cited

U.S. PATENT DOCUMENTS

| | | | |
|---|---|---|---|
| 2012/0016224 A1 | 1/2012 | Schmitt | |
| 2012/0271158 A1 | 10/2012 | Schmitt | |
| 2012/0296193 A1 | 11/2012 | Koktzoglou | |
| 2016/0249882 A1* | 9/2016 | Degertekin | ............... A61B 8/12 600/424 |

* cited by examiner

*Primary Examiner* — Reena Aurora
(74) *Attorney, Agent, or Firm* — Schiff Hardin LLP

(57) ABSTRACT

In a method and magnetic resonance (MR) apparatus for monitoring an interventional procedure with an intervention tool in a vessel of an examination subject, the intervention tool is moved in an insertion direction in the vessel and the position of a front end of the intervention tool in the insertion direction is determined. A first volume segment is determined dependent on the position and the flow direction of a fluid within the vessel. An RF saturation pulse is radiated into the first volume segment that saturates nuclear spins in the fluid within the first volume segment. MR data are acquired in a second volume segment, which contains the front end of the intervention tool and a region in front of the intervention tool in the insertion direction. An MR image is generated from the acquired MR data.

13 Claims, 3 Drawing Sheets

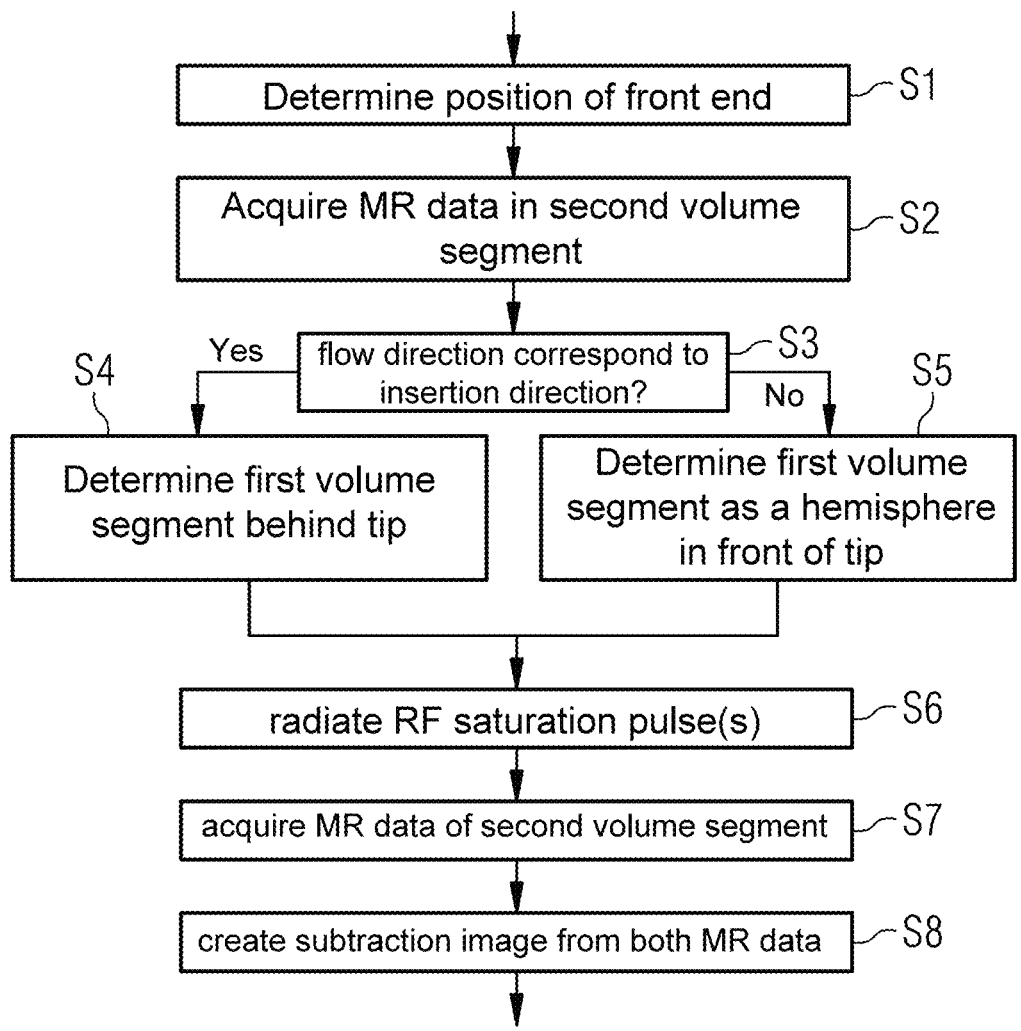

METHOD AND MAGNETIC RESONANCE APPARATUS FOR MONITORING AN INTERVENTIONAL PROCEDURE CONDUCTED WITH AN INTERVENTION TOOL

BACKGROUND OF THE INVENTION

Field of the Invention

The present invention concerns the monitoring of an interventional procedure with an intervention tool based on magnetic resonance (MR) images created by a magnetic resonance facility.

Description of the Prior Art

Catheter-based interventions play an increasingly important role in medical treatments and are used to an ever greater degree in neurovascular and cardiovascular interventions because they are so much less invasive than surgical interventions. Examples of catheter-based interventions include aneurysm coiling and stent insertion.

During a catheter-based interventional procedure, the intervention tool is generally fed through blood vessels to the treatment point. To this end the intervention tool is fed gradually from the entry point (generally in the patient's groin) through the blood vessels, the treating physician being able to control the wire by turning, twisting and pushing. In this process it is important to know not only the exact position of the wire tip or catheter (in other words the front end of the intervention tool), but more importantly also to be able to see the shape and configuration of the vessels located in front of the intervention tool in the insertion direction, in order to be able to take account of branches, bends, etc. when guiding the wire.

According to the prior art, a contrast agent is used to show the blood vessels. The contrast agent is released at the front end of the intervention tool (e.g. catheter tip) so that it is distributed with the fluid (blood) in the flow direction. The resulting contrast difference between the contrast agent and the fluid in the vessels without contrast agent shows the path of the vessels (at least for a short time).

The administration of contrast agents is generally always associated with a certain level of risk and breakdown of the contrast agent can have an adverse effect on patient health, specifically for patients with pre-existing illnesses. Therefore the administration of contrast agents is preferably kept to a minimum. This presents problems with low-field magnetic resonance facilities, because a higher dose of contrast agent generally has to be used with low-field magnetic resonance facilities than with high-field magnetic resonance facilities.

SUMMARY OF THE INVENTION

An object of the present invention is to implement monitoring of an interventional procedure with an intervention tool by a magnetic resonance facility without using a contrast agent.

The present invention provides a method for monitoring an interventional procedure with an intervention tool in a vessel of a living examination object. During the interventional procedure the intervention tool is moved in an insertion direction in the vessel. The inventive method has the following steps.

A position of a front end of the intervention tool is determined in a computer in the insertion direction within the vessel. In this step therefore the position of the front end of the intervention tool is determined, the front end being the end of the intervention tool furthest forward in the insertion direction, which, when the intervention tool is moved in the insertion direction, enters a region of the vessel, which no part of the intervention tool (e.g. a guide wire) has yet reached.

A first volume segment is determined in the computer as a function of the position of the front end of the intervention tool and the flow direction of the fluid (e.g. blood) within the vessel. As described in detail below, the first volume segment is determined such that the fluid present therein flows after a defined time period into vessel regions of the vessel located in front of the front end of the intervention tool in the insertion direction.

At least one RF saturation pulse is radiated into the first volume segment, in order thereby to saturate the fluid within the first volume segment, which flows to the position of the front end of the intervention tool in the flow direction in the vessel. The goal of saturating the spins in the first volume segment by the RF saturation pulse(s) is to saturate the spins of the fluid (e.g. blood), which then flow to the front end of the intervention tool. The RF saturation pulse(s) here must be determined and configured such that only the previously determined first volume segment is saturated by radiating the RF saturation pulse(s).

MR data are acquired within a second volume segment, which comprises the front end of the intervention tool and a region in front of the intervention tool in the insertion direction. This step is performed at a time so that at least some of the fluid that was saturated in the previous step has flowed into the second volume, so that the parts of the vessel located in the second volume segment contain the saturated fluid at the time when the MR data are acquired.

An MR image is produced from the acquired MR data. This MR image is reconstructed such that the saturated fluid within the vessel within the second volume segment stands out from the remainder of the MR image. The creation of this MR image is also known as Time-Of-Flight (TOF) non-CE MR angiography.

The MR image(s) created without the administration of contrast agent using the inventive method can be used to determine the location of the intervention tool in the vessel and also to show the part of the vessel in front of the intervention tool in the insertion direction. These MR images thus can be used to perform or control the guiding or forward movement of the intervention tool within the vessel, the shape and configuration of which is visible in the MR images, in an almost optimal manner.

Different methods can be used to determine the position of the front end of the intervention tool.

A firs such technique is to arrange one or more MR receive coils at a known point on the intervention tool. By acquiring the location of this/these MR receive coil(s) with the magnetic resonance facility using a predefined MR acquisition technique, it is possible with knowledge of the point on the intervention tool, at which the respective MR receive coil is located, to determine the position of the front end of the intervention tool.

Another technique is to use automatic pattern recognition in order to locate the intervention tool in a two-dimensional (including a projection image) or three-dimensional MR image, and thus the front end of the intervention tool, thereby determining the position of the front end.

If the intervention tool is a type known as an externally tracked intervention tool (in other words one that is monitored extracorporeally), its position, and therefore the position of the front end of the intervention tool, can be acquired by standard electromagnetic fields or direct current methods. Runtime differences or triangulation methods are used for position determination with such methods.

According to the invention, the determined position of the front end of the intervention tool serves to determine the first volume segment, in which the blood or fluid flowing to the front end of the intervention tool is saturated. The determined position of the front end of the intervention tool also is used to determine the location and alignment of the second volume segment, in which the region of the vessel, through which the intervention tool currently has to be guided, is located.

In an embodiment of the invention, the MR image is produced from the MR data acquired in the second volume segment, as a subtraction image, such as a subtraction image showing vessels with hyperintense contrast. Further MR data are also acquired in the second volume segment, before saturated spins flow into the second volume segment. The MR data acquired with saturated spins within the second volume segment can then be used to reconstruct a first MR image, while the further MR data can be used to reconstruct a second MR image. The MR image to be created can then be created as the difference between the first MR image and the second MR image.

With this embodiment, the further MR data acquired in the second volume segment before saturated spins flow into said second volume segment, can be seen as a type of reference dataset. This reference dataset and the MR data acquired with saturated spins within the second volume segments can then be used to create a subtraction image (in particular as the difference between the first and second MR images) with properties known to the person skilled in the art to show vessels (e.g. blood vessels) in the vicinity of the front end of the located intervention tool.

When determining the first volume segment, into which the at least one RF saturation pulse is radiated, a distinction is made between two instances.

1. The insertion direction, in which the intervention tool is moved forward in the vessel, corresponds to the flow direction of the fluid in the vessel.

2. The insertion direction is counter to the flow direction.

In the first instance the first volume segment is a vessel region of the vessel, which is situated behind the front end of the intervention tool counter to the insertion direction or flow direction. In other words in this embodiment the first volume segment is a cohesive volume, which extends within the vessel somewhere between the front end of the intervention tool and a point on the guide wire of the intervention tool, which is a certain distance from the front end.

For example the first volume segment can be cylindrical. In this embodiment the longitudinal direction of the first volume segment corresponds to the longitudinal direction of the vessel region of the vessel, through which the intervention tool is currently being moved or in which the intervention tool is presently located. The front end of the cylindrical first volume segment is located between the front end of the intervention tool and a point within the vessel region, which is a certain distance from the front end of the intervention tool. The cylindrical first volume segment here is configured in such a manner that it includes the vessel region. The cylindrical first volume segment therefore corresponds to what is known as a 1D bar, which is arranged as far as possible along the (already known part of the) vessel.

In the first instance, in which the flow direction of the fluid (blood) and the insertion direction or feed direction of the intervention tool correspond, spins in direct proximity to the front end of the intervention tool or as far as possible within the vessel behind the front end of the intervention tool counter to the insertion direction are saturated along the wire of the intervention tool. This ensures that in the subsequent inventive steps (acquiring MR data, creating an MR image) only the fluid from the vessel used for the interventional procedure is shown and therefore no interfering signals are acquired from vessels that happen to be located in the same projection direction.

It should be noted that the first volume segment can also be a slice (or a number of slices) through the vessel, which is (are) then saturated with a saturation pulse.

In the second instance, in which the flow direction of the fluid (blood) and the insertion direction of the intervention tool are counter to one another, the path of the vessel region of the vessel, from which the saturated spins flow to the front part of the intervention tool, is not known. Therefore it is more difficult to determine the first volume segment than in the first instance. According to the invention the following variants can be used to determine or configure the first volume segment in the second instance.

In a first variant, the first volume segment has a number of slices in front of the front end of the intervention tool in the insertion direction. Saturating the spins within these slices by radiating RF saturation pulses in causes the fluid in front of the front end of the intervention tool to be extensively saturated. This advantageously ensures that the spins of the fluid ultimately flowing to the front end of the intervention tool are also saturated.

In another variant, the first volume segment is determined as a volume segment that curves around the front end of the intervention tool in front of said front end of the intervention tool in the insertion direction. The first volume segment here can have any curvature, for example ellipsoid or hemispherical curvature. A first volume segment thus determined is preferred to the configuration of a first volume segment described above, as it allows local saturation of the spins, thereby minimizing signals from spins from vessels outside the region of interest in front of the front end of the intervention tool in the MR image to be created.

In a preferred inventive embodiment, acquiring the MR data is implemented in multiple acquisitions of MR data. Each time MR data are acquired in the second volume segment, a different time interval is selected between the radiating of the at least one RF saturation pulse and the respective acquisition of the MR data. MR data are then selected for the MR image reconstruction, in which the saturated spins are brightest in the region in front of the front end of the intervention tool in the insertion direction compared with the other acquired MR data.

In this embodiment MR data are selected to reconstruct the MR image in which the time period between the saturation step and the acquisition of the MR data is such that the saturated spins are most clearly visible in the region in front of the front end of the intervention tool in the created MR image compared with the other acquired MR data.

It is also possible to select the time interval between the saturation step (in other words the radiating of the at least one RF saturation pulse) and the acquisition of the MR data as a function of a flow speed of the fluid in the vessel to the front end of the intervention tool. This flow speed can be determined using a flowmeter arranged on the intervention tool or using (for example previously created) MR images.

Compared with the previous embodiment, in which a number of MR datasets are acquired, this embodiment, in which flow speed is used as a-priori information for selecting the coding (in particular the time interval between the saturation step and the acquisition of the MR data) appropriately, has the advantage of an accelerated workflow (shorter throughput time).

According to a further inventive embodiment acquiring MR data (and creating the MR image) includes acquiring the MR data in the form of a number of slices, one sectional image being created for each slice and a combination image being created from the sectional images. In this process each of the sectional images is individually coded (in other words each sectional image has its own coding), a coding assigned to a sectional image being used to code the pixels of the respective sectional image.

In this embodiment, at least two, preferably at least three, sectional images are recorded, in particular images of directly adjacent slices. It is preferably ensured that the slice direction (direction perpendicular to the slice) corresponds to the longitudinal direction of the vessel. When the sectional images are created from the MR data acquired for each slice, the pixels of the respective sectional image are given a coding assigned to said sectional image, in particular a color coding. The coding assigned to the sectional image advantageously allows the relative position of one sectional image within the sectional images to be determined.

The combining of the sectional images to create the combination image can take place here in the manner of a projection, so that the combination image is then a projection image. If the slice direction corresponds to the projection direction, the pixels of the sectional images behind one another in said projection direction can be combined with one another.

For example, if three sectional images are created, the top one being coded red, the center one white and the bottom one blue, if the front end of the intervention tool is shown as white, said front end is located within the center one of the three slices, from which the three sectional images were created. If however the front end is shown as blue or red in the combination image or projection image, the front end is located in the upper slice (in other words too high) or in the lower slice (in other words too low).

Thus the sectional image-specific coding allows slices to be tracked based on the way the front end of the intervention tool is shown in the combination image, for example to compensate for movement of the examination object or in particular movement of the intervention tool.

The present invention also encompasses a magnetic resonance facility having an MR data acquisition scanner with at least one RF antenna and a gradient coil arrangement, and an RF controller, a gradient controller, an image sequence controller, and a computer configured to monitor an interventional procedure with an intervention tool in a vessel of a living examination object. During the interventional procedure the intervention tool is moved in an insertion direction in the vessel. The magnetic resonance facility is designed to determine a position of a front end of the intervention tool within the vessel in the insertion direction and to determine a first volume segment as a function of the position and a flow direction of a fluid within the vessel by means of the computation unit. The magnetic resonance facility uses the RF controller to radiate at least one RF saturation pulse into the first volume segment in order to saturate the fluid within said first volume segment, which flows in the flow direction in the vessel to the previously determined position. The magnetic resonance facility uses the RF controller, the gradient controller and the image sequence controller to acquire MR data in a second volume segment, which contains the front end of the intervention tool and a region in front of the intervention tool in the insertion direction. The magnetic resonance facility creates an MR image based on the acquired MR data with the computer.

The advantages of the inventive magnetic resonance facility correspond essentially to the advantages of the inventive method, as described in detail above.

The present invention also encompasses a non-transitory, computer-readable data storage medium encoded with programming instructions (program code) that, when the storage medium is loaded into a computer or computer system of a magnetic resonance apparatus, cause the computer or computer system to operate the magnetic resonance apparatus so as to implement any or all embodiments of the method according to the invention, as described above.

The code can be a source code (e.g. C++), which still has to be compiled (translated) and linked or which only has to be interpreted, or an executable software code, which only has to be loaded into the corresponding computation unit or control facility to be executed.

The electronically readable data storage medium, e.g. a DVD, magnetic tape, hard disk or USB stick, on which electronically readable control information, in particular software (see above), is stored.

The present invention advantageously allows vessel paths in the vicinity of a front end or tip of an intervention tool to be shown without contrast agent based on MR images created using a magnetic resonance facility.

BRIEF DESCRIPTION OF THE DRAWINGS

FIG. 4 is a flowchart to explain inventive embodiments.

DESCRIPTION OF THE PREFERRED EMBODIMENTS

Figure 1:
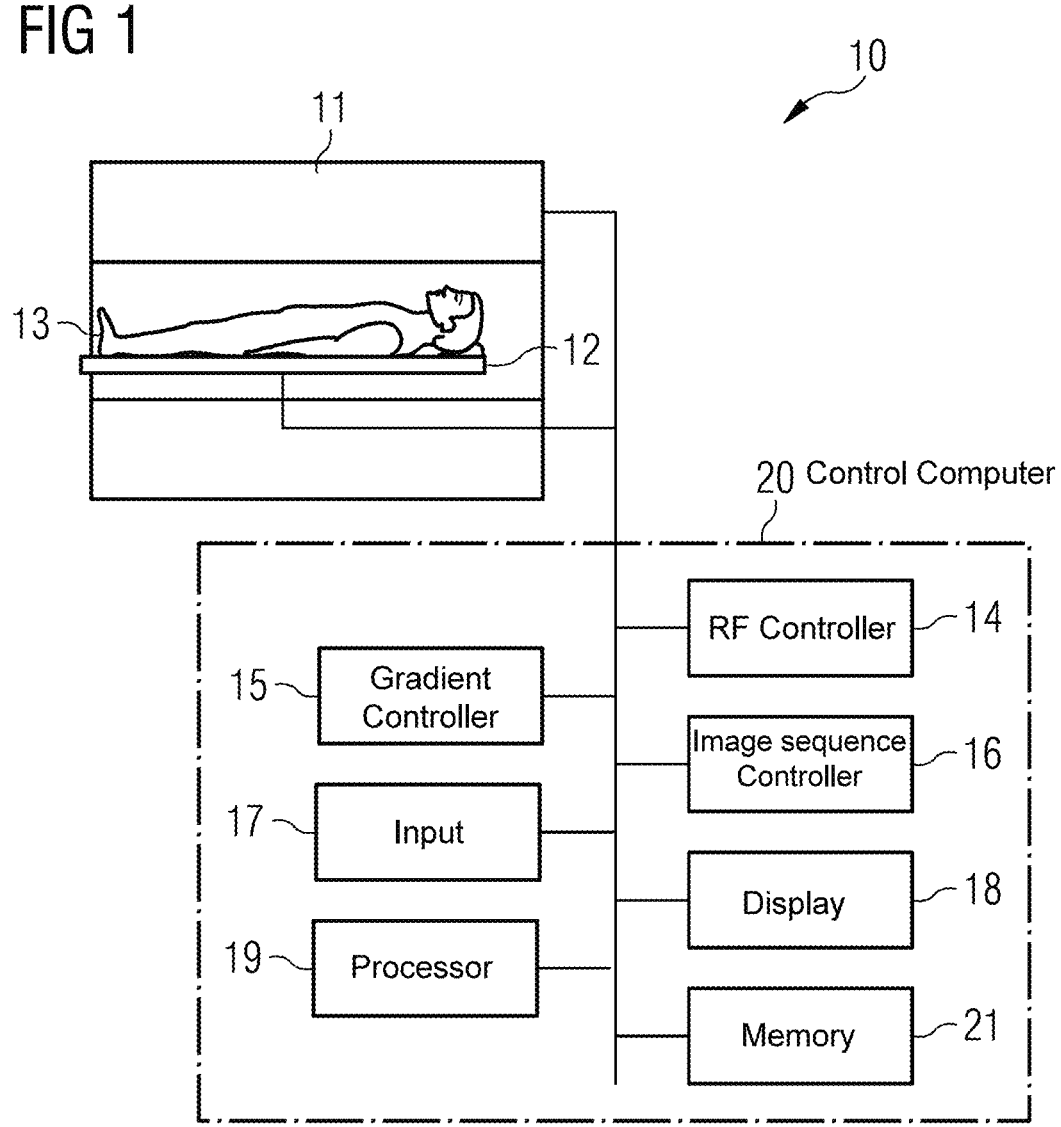
FIG. 1 a schematically illustrates an inventive magnetic resonance facility.

FIG. 1 shows a magnetic resonance facility 10 that, as explained below, can be used to monitor an interventional procedure with an intervention tool in a vessel of a living examination subject 13. The magnetic resonance facility 10 has a scanner 11 with a basic field magnet that generates a polarization field B0. An examination subject 13 being examined arranged on a bed 12 so as to be moved into the scanner 11, in order for spatially encoded magnetic resonance signals or MR data to be acquired from the examination subject 13. The RF coils used to record signals, for example a whole body coil or local coils, are not shown for clarity. Radiating radio-frequency pulses and switching magnetic field gradients causes the magnetization of certain nuclear spins in the examination subject 13 is to be deflected from the alignment produced by the polarization field B0, and the spatially encoded MR signals are detected by the RF reception coils. The manner in which MR images are generated by radiating the RF pulses and switching magnetic field gradients in different combinations and sequences is known to those skilled in the art, and thus need not be described in more detail herein.

The magnetic resonance facility 10 also has a control computer 20 that controls the magnetic resonance facility 10. The control computer 20 has a gradient controller 15 for controlling and switching the required magnetic field gradients. An RF controller 14 is provided for controlling and generating the RF pulses for deflecting the magnetization. An image sequence controller 16 controls the sequence of magnetic field gradients and RF pulses and therefore indirectly the gradient controller 15 and the RF controller 14. An operator can use an input unit 17 to enter inputs used to control the magnetic resonance facility 10, and MR images and other information required for control purposes can be displayed on a display unit 18. A computation processor 19 is provided for controlling the different units in the control computer 20 and for performing computational operations. A memory 21 is also provided, in which program modules and programs can be stored, used to control the operation of the magnetic resonance facility 10 when executed by the computation processor 19. The computation processor 19 is also configured to calculate MR images from the acquired MR signals.

Figure 2:
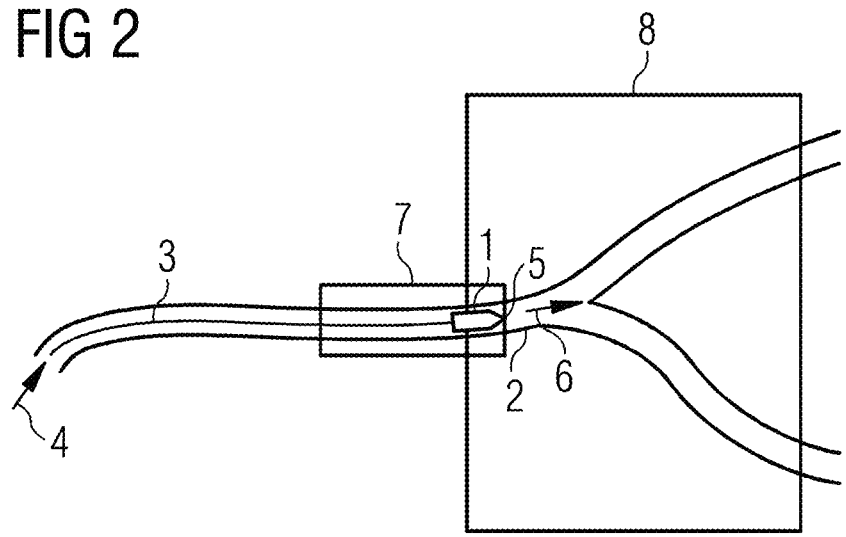
FIG. 2 shows an embodiment of the instance in accordance with the invention in which the insertion direction corresponds to the flow direction.

FIG. 2 explains the invention in the instance in which the insertion direction 4 of the intervention tool 1 within the vessel 2 corresponds to a flow direction 6 of a fluid (e.g. blood) within the vessel 2.

The interventional procedure with an intervention tool 1 in a vessel 2 is to be monitored by means of MR images. To this end the position of the tip or front end 5 of the intervention tool 1 within the vessel 2 is determined. Based on the position thus determined a cylindrical first volume segment 7 is determined, which comprises a part of the vessel, which is situated behind the front end 5 counter to the insertion direction 4.

Saturating the nuclear spins within this first volume segment 7 with one or more RF saturation pulses causes the fluid within the vessel part located within the first volume segment 7 also to be saturated. When a corresponding time after the radiating in of the RF saturation pulse(s) MR data is acquired in a second volume segment 8, which comprises the front end 5 of the intervention tool 1 and a region in front of the intervention tool 1 in the insertion direction 4, the fluid in the vessel regions of the vessel 2 within the second volume segment 8 is saturated, because the fluid has flowed from the first volume segment into these vessel regions during this time.

When this saturated fluid together with the front end 5 of the intervention tool 1 is shown in the form of an MR image, created from the MR data acquired in the second volume segment 8, the physician performing the interventional procedure can identify the path and branches of the vessel 2 in front of the intervention tool in the insertion direction 4 and thus control and plan the intervention.

Figure 3:
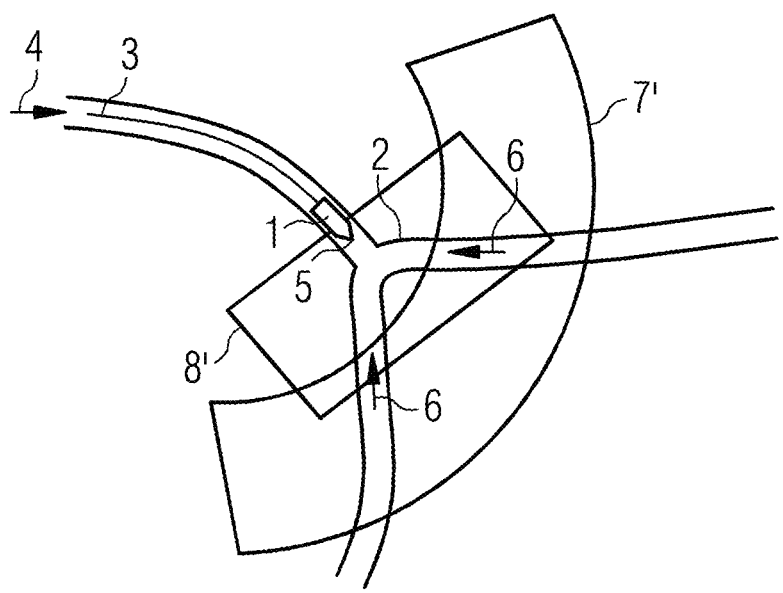
FIG. 3 shows an embodiment of the instance in accordance with the invention in which the insertion direction is counter to the flow direction.

FIG. 3 explains the invention in the instance in which the insertion direction 4 is counter to the flow direction 6 of the fluid in the vessel 2.

The position of the front end 5 of the intervention tool 1 is again determined. Based on this position in the inventive embodiment shown in FIG. 3 the first volume segment is configured as an arced or curved volume segment, in particular an ellipsoid volume segment, more specifically a hemispherical or spherical volume segment 7', which is curved around the front end 5 in front of the front end 5 (in other words the center point of the hemispherical volume segment 7' is on the same side of the hemispherical volume segments 7' as the front end 5 of the intervention tool 1).

According to the invention, the first volume segment 7' is configured such that any fluid flowing soon after in front of the front end 5 of the intervention tool 1 in the insertion direction 4 is located as far as possible within said first volume segment 7'. As the location and shape of the vessel regions of the vessel 2 in front of the front end 5 in the insertion direction 4 are not known (this will only be determined inventively), the first volume segment 7' must be correspondingly large.

The spins within the first volume segment 7' can either be saturated with an RF saturation pulse, which is specifically configured only to saturate the spins within said first volume segment 7'. However it is also possible to radiate a number of RF saturation pulses in at the same time in order to saturate only the spins within the first volume segment 7' with these RF saturation pulses radiated in parallel.

When (as in FIG. 2) a corresponding time after the radiating in of the RF saturation pulse(s) MR data is acquired in a second volume segment 8', which contains the front end 5 of the intervention tool 1 and a region in front of the intervention tool 1 in the insertion direction 4, all the fluid in the vessel regions of the vessel 2 within the second volume segment 8 should be saturated, as the fluid that has flowed into said vessel regions has flowed in from the first volume segment 7'.

When this saturated fluid, which has flowed into the vessel regions of the vessel 2 in front of the front end 5 in the insertion direction 4, is shown together with the front end 5 in the form of an MR image, which is reconstructed by means of the MR data acquired in the second volume segment 8', it is possible to identify the shape and configuration of the vessel 2 in front of the intervention tool 1 in the insertion direction 4.

FIG. 4 shows a flowchart to explain the inventive embodiments.

In step S1 the position of the tip or front end 5 of the intervention tool 1 is determined.

In order to acquire a reference dataset, in step S2 MR data is acquired in the second volume segment 8, 8', which comprises the front end 5 of the intervention tool 1 and a region in front of said front end 5 in the insertion direction 4.

Determination of the position of the front end 5 in the preceding step S1 can also be performed for example based on the MR data acquired in step S2 (in particular by means of an MR image reconstructed therefrom).

In step S3 a distinction is made between the two instances—whether the flow direction 6 corresponds to the insertion direction 4 or is counter to the insertion direction 4.

If the flow direction 6 and the insertion direction 4 are the same, in step S4 the first volume segment 7, 7' behind the tip 5 counter to the insertion direction 4 is determined or located along the intervention tool 1. If however the flow direction 6 and insertion direction 4 are counter to one another, the first volume segment 7, 7' is determined or located as a hemisphere in front of the tip 5 in the insertion direction 4.

In step S6 the spins within the first volume segment are saturated by radiating in one or more RF saturation pulses.

In step S7 MR data of the second volume segment 8, 8' is acquired. The acquisition of said MR data here takes place a defined time period after the saturation step S6, so that during this time period saturated spins of the fluid in the vessel 2 can flow out of the first volume segment 7, 7' into the vessel regions of the vessel 2 in front of the front end 5 of the intervention tool 1.

In step S8 a subtraction image is created from the MR data acquired in steps S2 and S7, in order to show the vessel regions of the vessel 2 in the vicinity of the tip 5 of the intervention tool 1 based on the subtraction image.

The steps shown in FIG. 4 are performed continuously to monitor an interventional procedure with the intervention tool 1 in the vessel 2. It is of course known for each interventional procedure whether or not the flow direction 6 corresponds to the insertion direction 4, so that when the inventive method is performed, it is only determined once for all iterations whether step S4 or step S5 has to be performed.

To determine the position of the tip 5 of the intervention tool 1 in step S1 it is also possible, for example, to use an MR image, which is created based on the MR data acquired in the previously performed step S7.

In order to verify the location of the tip 5 of the intervention tool 1 based on inventive sectional images with sectional image-specific coding, said sectional images can be created based on MR data acquired in step S2 or S7.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for monitoring an interventional procedure of a subject conducted with an intervention tool in a vessel, in which a fluid flows, while the subject is situated in a magnetic resonance (MR) data acquisition scanner, wherein the intervention tool is moved in an insertion direction in the vessel during the interventional procedure, said method comprising:

detecting a position of a front end of the intervention tool in the insertion direction within the vessel;

providing an electronic designation of the detected position of the front end of the interventional tool to a processor and, in said processor, determining a first volume segment of the examination subject dependent on said position and dependent on a flow direction of said fluid within the vessel;

from said processor, operating the MR data acquisition scanner so as to radiate at least one radio-frequency (RF) saturation pulse into said first volume segment, and thereby saturating nuclear spins of the fluid within the first volume segment, said fluid in which the nuclear spins are saturated flowing to said detected position in said flow direction in said vessel;

in said processor, determining a second volume segment comprising said front end of said intervention tool and a region in front of said front end of said intervention tool in the insertion direction;

from said processor, operating the MR data acquisition scanner so as to acquire MR data in said second volume segment; and in said processor, reconstructing image data from the acquired MR data and displaying said image data at a display as a depiction of said front end of said intervention tool and said region in front of said front end of said intervention tool.

2. A method as claimed in claim 1 comprising detecting said position of said front end of said intervention tool by locating at least one MR reception coil of said MR scanner using a predetermined MR acquisition technique, said at least one MR reception coil being situated at a known point on said intervention tool, with the position of the front end of the intervention tool being determined in said processor dependent on said position of said at least one MR reception coil.

3. A method as claimed in claim 1 wherein said MR data are first MR data, and wherein said method comprises:

from said processor, operating said MR data acquisition scanner to acquire further MR data from the second volume segment, before the saturated nuclear spins of said fluid flow into said second volume segment;

reconstructing a first MR image using said first MR data, reconstructing a second MR image using said further MR data; and generating said image that is depicted on said display as a difference between said first MR image and said second MR image.

4. A method as claimed in claim 1 wherein said insertion direction corresponds to said flow direction, and wherein said first volume segment comprises a part of said vessel that is situated behind said front end of said intervention tool, opposite to said insertion direction.

5. A method as claimed in claim 4 wherein said first volume segment is cylindrical, and has a longitudinal direction, and wherein said longitudinal direction of said first volume segment corresponds to a longitudinal direction of said part of said vessel.

6. A method as claimed in claim 1 wherein said insertion direction is opposite to said flow direction, and wherein said first volume segment comprises a plurality of slices situated in front of said front end of said intervention tool in said insertion direction.

7. A method as claimed in claim 1 wherein said insertion direction is opposite to said flow direction, and wherein said first volume segment curves around said front end of said intervention tool in front of said front end in said insertion direction.

8. A method as claimed in claim 7 wherein said first volume segment is hemispherical.

9. A method as claimed in claim 1 comprising:

from said processor, operating said MR data acquisition scanner to acquire said MR data in multiple acquisitions, with a different time interval in each respective acquisition between radiation of said at least one RF saturation pulse and the acquisition of the MR data in that respective acquisition; and reconstructing said image data by selecting MR data, among the MR data acquired in said multiple acquisitions, in which the saturated nuclear spins appear brightest at said front end of said intervention tool, for use as said image data in the image depicted at said display.

10. A method as claimed in claim 1 comprising selecting a time interval between radiation of said at least one RF saturation pulse and the acquisition of said MR data dependent on a flow speed of said fluid in said vessel relative to said front end of said intervention tool.

11. A method as claimed in claim 1 comprising from said processor, operating the MR data acquisition scanner to acquire said MR data in a plurality of slices, and reconstructing sectional image data respectively for each slice, and generating a combination image from said sectional images and displaying image data corresponding to said combination image as said image depicted at said display; and giving each sectional image a sectional image-specific coding, and giving respective pixels in the respective sectional images and individual coding corresponding to the coding for the image-specific coding in which the pixels are present.

12. A magnetic resonance (MR) apparatus for monitoring an interventional procedure conducted with an intervention tool in a vessel, in which a fluid flows, wherein the intervention tool is moved in an insertion direction in the vessel during the interventional procedure, said MR apparatus comprising:

an MR data acquisition scanner in which the subject is situated during the interventional procedure;

a position detector that detects a position of a front end of the intervention tool in the insertion direction within the vessel;

a processor provided with an electronic designation of the detected position of the front end of the intervention tool from said position detector, said processor being configured to determine a first volume segment of the examination subject dependent on said position and dependent on a direction of said flow of said fluid within the vessel;

said processor being configured to operate the MR data acquisition scanner so as to radiate at least one radio-frequency (RF) saturation pulse into said first volume segment, and thereby saturate nuclear spins of the fluid within the first volume segment, said fluid in which the nuclear spins are saturated flowing to said detected position in said flow direction in said vessel;

said processor being configured to determine a second volume segment comprising said front end of said intervention tool and a region in front of said front end of said intervention tool in the insertion direction;

said processor being configured to operate the MR data acquisition scanner so as to acquire MR data in said second volume segment; and said processor being configured to reconstruct image data from the acquired MR data and to display said image data at a display as a depiction of said front end of said intervention tool and said region in front of said front end of said intervention tool.

13. A non-transitory, computer-readable data storage medium encoded with programming instructions, said storage medium being loaded into a computer of a magnetic resonance (MR) apparatus, having an MR data acquisition scanner in which a subject is situated, said programming instructions causing said computer to monitor an interventional procedure of the subject conducted with an intervention tool in a vessel, containing fluid flowing in a flow direction, said intervention tool being moved in an intervention direction in the vessel during the interventional procedure while the subject is situated in the MR data acquisition scanner, by:

receiving an electronic designation of a detected position of the front end of the interventional tool and determining a first volume segment of the examination subject dependent on said position and dependent on a direction of said flow of said fluid within the vessel;

operating the MR data acquisition scanner so as to radiate at least one radio-frequency (RF) saturation pulse into said first volume segment, and thereby saturating nuclear spins of the fluid within the first volume segment, said fluid in which the nuclear spins are saturated flowing to said detected position in said flow direction in said vessel;

determining a second volume segment comprising said front end of said intervention tool and a region in front of said front end of said intervention tool in the insertion direction;

operating the MR data acquisition scanner so as to acquire MR data in said second volume segment; and reconstructing image data from the acquired MR data and displaying said image data at a display as a depiction of said front end of said intervention tool and said region in front of said front end of said intervention tool.

* * * * *